US00PP23520P2

(12) United States Plant Patent
Hanes

(10) Patent No.: US PP23,520 P2
(45) Date of Patent: Apr. 9, 2013

(54) ***VERBENA* PLANT NAMED 'VEAZ0005'**

(50) Latin Name: *Verbena×hybrida*
Varietal Denomination: VEAZ0005

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 20 days.

(21) Appl. No.: 13/317,561

(22) Filed: Oct. 22, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt
(74) *Attorney, Agent, or Firm* — Joshua L. Price

(57) ABSTRACT

A new *Verbena* plant named 'VEAZ0005' particularly distinguished by the large lighter red-purple colored flowers, an upright habit and well branched growth.

1 Drawing Sheet

Latin name of the genus and species of the plant claimed: *Verbena×hybrida*.

Varietal denomination: 'VEAZ0005'.

BACKGROUND OF THE NEW PLANT

The present invention comprises a new *Verbena*, botanically known as *Verbena×hybrida*, and hereinafter referred to by the variety name 'VEAZ0005'.

'VEAZ0005' is a product of a planned breeding program. The new cultivar has large lighter red-purple colored flowers, an upright habit and well branched growth.

'VEAZ0005' originated from a cross pollinated hybridization made in the summer of 2007 in a controlled breeding environment in Gilroy, Calif., USA. The female parent was the unpatented, proprietary plant designated '2043-2' with lavender pink flowers, a more spreading than upright habit and less vigor.

The male parent of 'VEAZ0005' was 'Lan Upbriro', U.S. Plant Pat. No. 20,709, with deep rose flowers, less seed set and smaller flowers. The resultant seed was sown in January 2008.

'VEAZ0005' was selected as one flowering plant within the progeny of the stated cross in April 2008 in a controlled environment in Gilroy, Calif., USA.

The first act of asexual reproduction of 'VEAZ0005' was accomplished when vegetative cuttings were propagated from the initial selection in April 2008 in a controlled environment in Gilroy, Calif., USA.

BRIEF SUMMARY OF INVENTION

Horticultural examination of plants grown from cuttings of the plant initiated in April 2008, and continuing thereafter, has demonstrated that the combination of characteristics as herein disclosed for 'VEAZ0005' are firmly fixed and are retained through successive generations of asexual reproduction.

'VEAZ0005' has not been observed under all possible environmental conditions. The phenotype may vary significantly with variations in environment such as temperature, light intensity and day length.

A Plant Breeder's Right for this cultivar was applied for in Canada on Dec. 24, 2010, #10-7145. 'VEAZ0005' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

Figure 1:
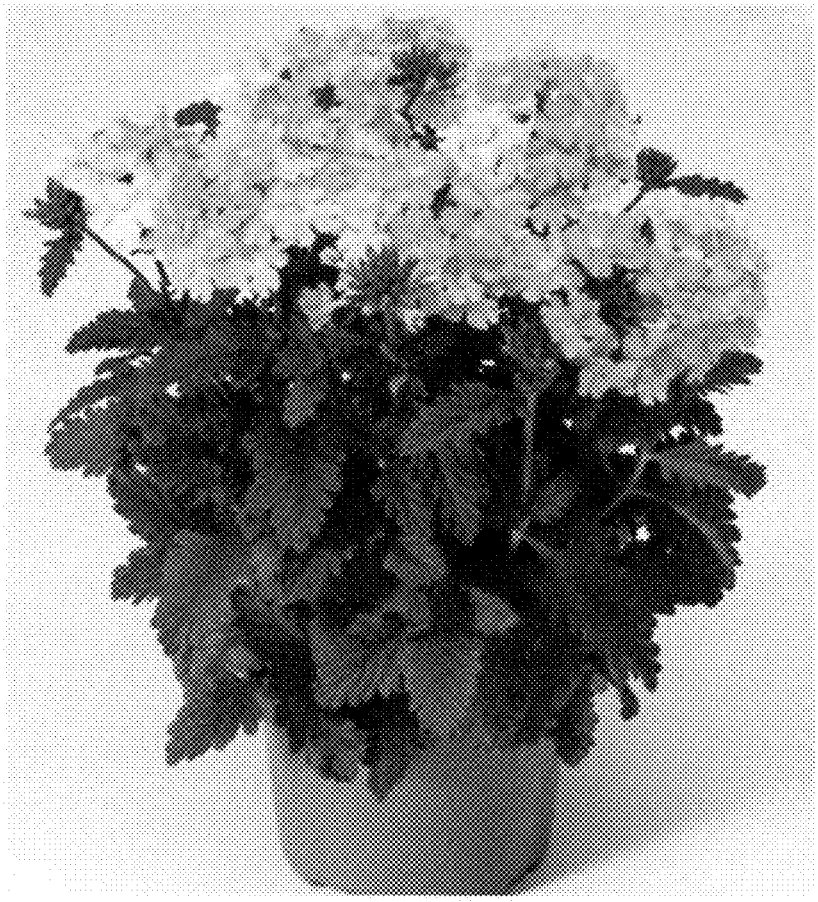
Figure 2:
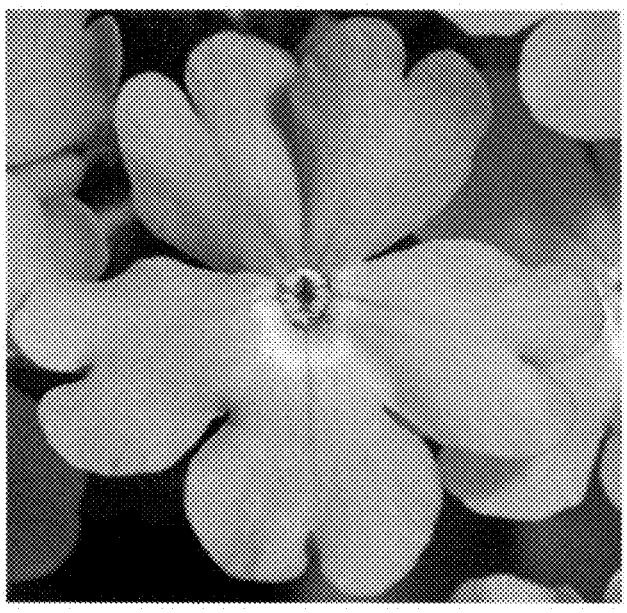

The accompanying photographic drawing shows typical flower and foliage characteristics of 'VEAZ0005' with colors being as true as possible with an illustration of this type. The photographic drawings show in FIG. 1. a flowering plant of the new variety, and in FIG. 2. a close-up of the flowers.

DETAILED BOTANICAL DESCRIPTION

The aforementioned photographs were taken in April 2010 from plants grown in a greenhouse trial in Enkhuizen, The Netherlands. These plants were growing in 12 cm pots and were approximately 12 weeks of age. The close-up photograph was taken in April 2011 in Gilroy, Calif. Plants were about 9-11 weeks of age grown in a greenhouse breeder's trial.

The plant descriptions and measurements were taken in May 2011 in Enkhuizen, The Netherlands on about 13 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'VEAZ0005' AND A SIMILAR VARIETY

| | 'VEAZ0005' | 'Lan Upbriro' (U.S. Plant Pat. No. 20,709) |
|---|---|---|
| Seed set: | More seed set | Less seed set |
| Flower size: | Larger | Smaller |
| Flower color: | Pink | Deep rose |

Plant:

*Form, growth and habit*.—Herbaceous, upright and well branched.

*Plant height*.—About 16.0 cm.

*Plant height* (*inflorescence included*).—About 23.0 cm.

*Plant width*.—About 28.0 cm.

Roots:

*Number of days to initiate and produce roots*.—About 10-14 days at about 22 degrees C.

*Type*.—Fine, fibrous, free branching.

*Color*.—RHS N155B.

Foliage:

*Arrangement*.—Opposite.

*Immature, leaf color, upper surface*.—RHS 137C.

*Lower surface*.—Between RHS 138B and RHS 138C.

*Mature, leaf color, upper surface*.—RHS 137A.

*Lower surface*.—RHS 138D.

*Length*.—4.5 cm.

*Width*.—3.0 cm.

*Shape*.—Ovate.

*Base shape*.—Attenuate.

*Apex shape*.—Apiculate.

*Margin*.—Dentate, pinnatifid.

*Texture, upper surface*.—Short hair.

*Lower surface*.—Short, stiff hair mainly along the veins; some glandular hairs.

*Color of veins, upper surface*.—RHS 145B.

*Color of veins, lower surface*.—RHS 145C.

*Petiole color*.—RHS 145B; with RHS 145C on the under side.

*Length*.—0.1-0.4 cm.

*Diameter*.—0.1-0.3 cm.

*Texture*.—Hirtellous.

Stem:

*Characteristics*.—Side branches develop potentially at every node.

*Color of stem*.—RHS 145A.

*Length of stem*.—Approximately 16.0-18.0 cm.

*Diameter*.—0.2 cm.

*Length of internodes*.—Approximately 3.0-6.0 cm.

*Texture*.—Rough; densely covered with hair; hirsute.

*Color of peduncle*.—RHS 145A.

*Length of peduncle*.—Most often 1.0-5.5 cm.

*Peduncle diameter*.—0.2 cm.

*Texture*.—Rough, densely covered with short glandular hair; hirtellous.

Inflorescence:

*Type*.—Umbel-like, but actually a spike, umbrella-shaped to roughly semi-spherical.

*Blooming habit*.—Flowers continuously.

*Quantity of inflorescences per plant*.—Approximately 26.

*Lastingness of individual blooms on the plant*.—New florets continue to open in one spike over a period of 14 days in the greenhouse.

*Fragrance*.—Very little.

*Inflorescence horizontal diameter*.—6.0 cm.

*Inflorescence depth* (*height*).—2.5 cm.

*Quantity of flowers and buds per inflorescence*.—Approximately 20.

Bud (just when starting to show color):

*Color*.—RHS 63D.

*Length*.—2.2 cm.

*Width*.—0.7 cm.

*Shape*.—Mainly tube-shaped with a bulbous end.

Floret:

*Form and type*.—Sessile; salverform, composed of 5 partly fused petals with a base of a narrow tube.

*Immature color, upper surface*.—RHS N57C to RHS N57D.

*Lower surface*.—RHS 62 C to RHS 62D.

*Mature color, upper surface*.—RHS N57C to RHS N57D.

*Lower surface*.—RHS 62C.

*Eye size*.—0.4 cm.

*Eye color*.—RHS 155D but white with RHS 157C to 154D at the corolla opening.

*Floret diameter*.—2.0 cm.

*Floret depth*.—1.4-2.0 cm.

*Length of petals*.—1 cm.

*Width of petals*.—0.9 cm.

*Petal shape*.—Obcordate.

*Apex shape*.—Emarginate.

*Margin*.—Entire.

*Petal texture, upper surface*.—Smooth and glabrous.

*Lower surface*.—Smooth and glabrous.

*Corolla tube length*.—1.4-2.0 cm.

*Corolla tube color inside*.—RHS 150C.

*Tube color outside*.—RHS 145D.

*Corolla texture, inside*.—Glabrous.

*Outside*.—Glabrous basally; glandular hairs at the flare.

Calyx:

*Type*.—Five sepals whose margins are fused to each other along their length, with a transparent membrane of less than 0.1 cm in width and with one smaller sepal attached to the base of the calyx.

*Color of sepals*.—RHS 144B with RHS 60C on the apex.

*Length of sepals*.—1.3 cm.

*Width of sepals*.—0.1 cm.

*Sepal shape*.—Linear, fused.

*Apex shape*.—Acute.

*Margins*.—Entire.

*Texture*.—Densely covered with short hair.

Reproductive organs:

*Pistil*.—1.

*Length*.—1.7 cm.

*Style color*.—RHS 144D.

*Style length*.—1.6 cm.

*Stigma color*.—RHS 144A.

*Stamens*.—Anthers and filaments fused to upper half of corolla tube; four anthers with two pollen sacs per anther.

*Color of filaments*.—RHS 150D to RHD 155B.

*Length filaments*.—0.1 cm.

*Anther color*.—RHS 1B.

*Length of anthers*.—0.1-0.15 cm.

*Color of pollen*.—RHS 2A.

*Pollen amount*.—Little.

*Fertility/seed set*.—Moderate seed set.

*Disease/pest resistance*.—Has not been observed on this hybrid.

What is claimed is:

1. A new and distinct variety of *Verbena* plant named 'VEAZ0005' substantially as illustrated and described herein.

* * * * *